United States Patent [19]

Khandelwal et al.

[11] Patent Number: 5,250,682
[45] Date of Patent: Oct. 5, 1993

[54] PROCESS FOR THE PREPARATION OF 6-[3-SUBSTITUTEDAMINOPROPIONYL]-7-DEACETYLFORSKOLIN DERIVATIVES

[75] Inventors: Yatendra Khandelwal; Bansi Lal; Jürgen Blumbach, all of Bombay, India

[73] Assignee: Hoechst Aktiengesellschaft, Frankfurt am Main, Fed. Rep. of Germany

[21] Appl. No.: 733,812

[22] Filed: Jul. 22, 1991

[30] Foreign Application Priority Data

Jul. 24, 1990 [EP] European Pat. Off. ............ 90114125

[51] Int. Cl.$^5$ .................. C07D 405/02; C07D 311/92
[52] U.S. Cl. ..................................... 540/596; 549/389; 544/150; 544/375; 546/196; 548/517; 548/525
[58] Field of Search ........................ 549/389; 540/596; 544/150, 375; 546/196; 548/517, 525

[56] References Cited

U.S. PATENT DOCUMENTS

| | | | |
|---|---|---|---|
| 4,639,446 | 1/1987 | Kosley et al. | 549/389 |
| 4,883,793 | 11/1989 | Kosley et al. | 549/389 |
| 5,041,565 | 8/1991 | Kosley et al. | 549/389 |

FOREIGN PATENT DOCUMENTS

| | | |
|---|---|---|
| 63270 | 4/1987 | Australia . |
| 0193132 | 9/1986 | European Pat. Off. . |
| 0217372 | 4/1987 | European Pat. Off. . |
| 0222413 | 5/1987 | European Pat. Off. . |
| 0294695 | 12/1988 | European Pat. Off. ............ 549/389 |
| 163242 | 8/1988 | India . |
| 164675 | 5/1989 | India . |
| 0009986 | 1/1989 | Japan .................. 549/389 |
| 87/5043 | 1/1988 | South Africa . |
| 88/8194 | 7/1989 | South Africa . |

OTHER PUBLICATIONS

Laurenza, A., et al., "Stimulation of Adenylate Cyclase by Water-Soluble Analogues of Forskolin", Molecular Pharmacology, 32:133–39 (1987).

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

Process for the manufacture of 6$\beta$-(3-substituted amino)propionyloxy-7-deacetyl-forskolin derivatives of the general formula

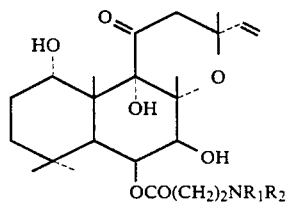

6 Claims, No Drawings

PROCESS FOR THE PREPARATION OF 6-[3-SUBSTITUTEDAMINOPROPIONYL]-7-DEACETYLFORSKOLIN DERIVATIVES

The present invention relates to a novel process for the preparation of 6β-(3-substitutedaminopropionyl)-7-deacetyl-forskolin derivatives of high pharmacological interest represented by the general formula I,

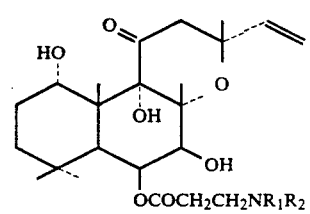

wherein $R_1$ and $R_2$ each stands for hydrogen, alkyl, aryl, aralkyl or dialkylaminoalkyl; or $R_1$ and $R_2$ together with the nitrogen to which they are attached form a heterocycle which may contain an additional heteroatom such as N, O, S and may optionally be substituted at one or more positions by groups such as alkyl, alkoxy, hydroxyl, halogen or aryl and pharmaceutically acceptable salts thereof. Such compounds are of high interest especially because of compound NKH-477, a 6 - substitutedaminopropionylforskolin derivative, which is very useful in the treatment of congestive heart failure.

The term alkyl stands for a $C_1$-$C_6$, preferably $C_1$-$C_4$ straight or branched chain such as methyl, ethyl, propyl, isopropyl, n-butyl, tert. butyl or n-pentyl.

The term aryl stands for phenyl, optionally substituted with groups such as $C_1$-$C_4$-alkyl, $C_1$-$C_4$-alkoxy, hydroxyl, halogen such as chlorine or fluorine, nitro, cyano or trifluoromethyl.

The term aralkyl stands for benzyl, wherein phenyl has the same meanings defined above.

The term dialkylaminoalkyl stands for groups such as for example dimethylaminopropyl or diethylaminobutyl.

The term heterocycle stands for groups such as e.g. morpholino, piperidino, pyrrolidino, piperazino or homopiperidino, which may be substituted preferably by $C_1$-$C_4$-alkyl.

Pharmaceutically acceptable salts means salts of inorganic and organic acids such as hydrochloric acid, hydrobromic acid, sulphonic acid, phosphoric acid, formic acid, acetic acid, maleic acid, citric acid, tartaric acid, lactic acid, methane-sulphonic acid.

Prior Art

Compounds of the formula I belong to the series of water-soluble aminoacyl forskolin derivatives which display potent pharmacological properties. They are the subject of different patent applications and publications viz. EP application No. 0222413, E.P. Application No. 0193132; Indian Patent No. 163242, Ger. Appl. No. P 3535086.5; Indian Pat. Appl. No. 164675, Ger. Pat. appln. No. 3623300-5; J. P. Appln. No. 159638; Ind. Pat. Appln. No. 238/BOM/87, Ger. Pat. Appl. No. 3737353.6, Mol. Pharmacol., 32, 133 (1987). Processes for their preparation can be summarised as below:

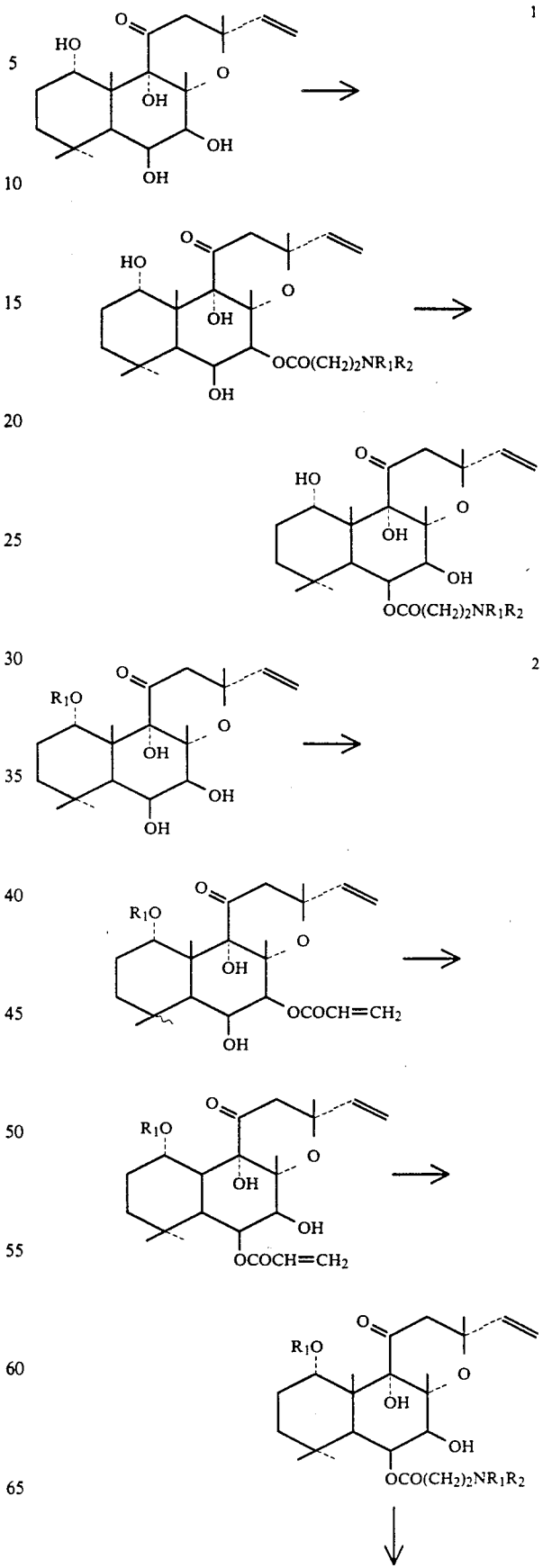

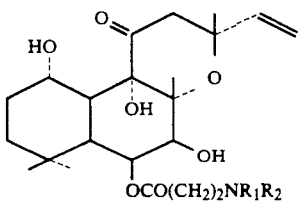

As the sequences show, compounds of formula I are prepared (a) directly, without the use of protecting groups at the 1-OH or 1-OH/9-OH positions, which results into the formation of formula I along with 1, 6-diacylated compound. Separation of these compounds was tedious.

(b) by protecting the 1-OH group with a protecting group such as t-butyldimethylsilyl or methoxyethoxymethyl, and removing the protecting group at an appropriate stage (Patent Nos. E.P. 0193132 and E.P. 0222413).

(c) by protecting the 1-OH group together with 9-OH group with groups such as carbonyl (C=O), thiocarbonyl (C=S), CHNRR', and removing the 1,9-protecting group at an appropriate stage (Patent No. E.P. 0193132).

All the processes of the prior art have several disadvantages:

(a) Those processes in which direct acylation of the 7-OH group is followed by migration to 6-position. These involve 2-3 steps and also use of anhydrous amine.

(b) Those processes in which protection of 1-OH and/or 9-OH is mentioned, the number of steps is increased i.e. initial protection and then in the last step deprotection of the 1-OH and/or 9-OH group.

Inventiveness and Detailed Description of the Present Invention

In the present invention, it has now been surprisingly found that compounds of the formula I can be prepared from 7-deacetylforskolin II,

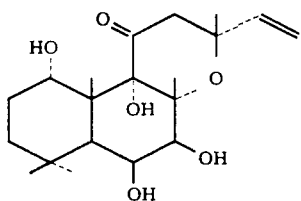

in a one-pot reaction sequence, by treatment of II (1 eq) with a 3-halo-propionyl halide (1.1-3.0 eq) in the presence of an organic base such as e.g. pyridine, diisopropyl ethylamine or triethylamine, preferably triethylamine, (4-50 eq), in an aprotic solvent such as e.g. chloroform, dichloromethane, toluene or xylene, preferably toluene, at a temperature of about 0°-1200° C., subsequently concentrating the reaction mixture under vacuo to dryness, addition of a water miscible solvent such as e.g. Tetrahydrofuran, dioxane or acetonitrile preferably acetonitrile and water, and an aqueous base such as e.g. aqueous KOH, aqueous NAOH (1-5 eq), followed by addition of an appropriate amine or an aqueous solution of an appropriate amine in excess of about 1 eq, for example an aqueous solution of e.g. dimethylamine, piperidine, morpholine or N-methylpiperazine, leading to the desired 6$\beta$-(3-substituted amino propionyl)-7-deacetyl-forskolin derivatives. These derivatives can be optionally converted to pharmaceutically acceptable salts.

The inventiveness of the above process for the preparation of 6$\beta$-[3-substitutedaminopropionyl]-7-deacetylforskolin derivatives lies in (a) no step being needed for protection of hydroxy groups, (b) a one-pot reaction process, thus rendering it simple and economical and (c) use of simple, commercially available reagents, such as aqueous dimethylamine. It could not be expected, that especially steps (a) and (b) would be practicable.

The above conditions were developed with a view to run the process in good yield, with low costs and with minimized industrial hazards.

More specifically, the present invention describes a process for preparation of 6$\beta$-[3-dimethylaminopropionyl]-7-deacetylforskolin which comprises treatment of 3-chloropropionylchloride (1.1-3.0 eq) with 7-deacetylforskolin (1 eq) of the formula II in the presence of an organic base such as triethylamine (4-50 eq) in an aprotic solvent such as toluene at temperatures ranging from about 0° C. at the beginning of the reaction to ambient temperature at the end of the reaction for a period of about 1.5 to 3 hours, preferably 1.5 hours, or a temperature range of about 0°-120° C. throughout the reaction period, subsequent concentration in vacuo of the reaction mixture to dryness, followed by addition to the residue of aqueous acetonitrile preferably in the ratio of acetonitrile:water of 8:7 and aqueous sodium hydroxide preierably of 1N concentration, stirring at ambient temperatures for a period from about 24 hours to 80 hours preferably 72 hours and finally addition of the desired amine (anhydrous or aq. solution) to the reaction mixture and continuing the stirring for an additional two to four hours to obtain the desired product.

The following examples are provided to serve only as an illustration of how the process is to be worked, without being exclusive of other compounds of the invention that may be so prepared.

EXPERIMENTAL

6$\beta$-(3-dimethylaminopropionyl)-7-deacetylforskolin (1)

3-Chloropropionylchloride (1 ml) was added to a mixture of 7-deacetylforskolin (2.0 g), toluene (100 ml) and dry triethylamine (4 ml) at 0° C. The reaction mixture was stirred at ambient temperature to 120° C. for 1.5 hrs. and concentrated under vacuo.

The residue was taken in acetonitrile:water (8:7, 150 ml), and 1N sodiumhydroxide (17 ml) was added to the above solution. The reaction mixture was stirred-at ambient temperature for 3 days and aqueous dimethylamine (30-40%, 40 ml) was added. The reaction mixture was further stirred for 2 hours at ambient temperature and extracted with ethyl acetate. The organic layer was washed, dried over anhydrous sodium sulphate and concentrated. The residue on purification by chromatography yielded the desired compound. Yield ~1.4 g. m.p. 140°-142° C.

Similarly, the following compounds were prepared by using the appropriate amine.

2. 6$\beta$-(3-N-methylpiperazinopropionyl)-7-deacetylforskolin. m.p. 187°-189° C.

3. 6$\beta$-(3-piperidinopropionyl)-7-deacetylforskolin. m.p. 149°-150° C.

4. 6$\beta$-(3-morpholinopropionyl)-7-deacetylforskolin. m.p. 188°-190° C.

TABLE 1
PMR DATA FOR THE ABOVE WORKINGS EXAMPLES

1. $NR_1R_2 = -NMe_2$
   PMR (CDCl$_3$): δ = 6.08(d of d, $J_{cis}$=10.8Hz, $J_{trans}$=18Hz, vinylic-$\underline{H}$), 5.9(d of d, $J_{6,7}$=4.5Hz, $J_{5,6}$=3Hz, 6-C$\underline{H}$), 5.18(d of d, $J_{trans}$=18Hz, $J_{gem}$=2Hz, vinylic-$\underline{H}$), 4.94(d of d, $J_{cis}$=10.8Hz, $J_{gem}$=2Hz, vinylic-$\underline{H}$), 4.56(bs, 1-C$\underline{H}$), 4.19(d, J=4.5Hz, 7-C$\underline{H}$), 3.32 (d, $J_{gem}$=17Hz, 12-CH), 2.7-2.2(m, COC$\underline{H}_2$, N—CH2, 12-C$\underline{H}$), 2.3(s, N—C$\underline{H}_3$), 1.6, 1.46, 1.42, 1.14, 1.0(s, 5×C$\underline{H}_3$).

2. 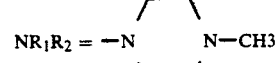
   $NR_1R_2 = -N\phantom{xx}N-CH3$

PMR (CDCl$_3$): δ = 6.08(d of d, $J_{cis}$=10.8Hz, $J_{trans}$=18Hz, vinylic-$\underline{H}$), 5.9(d of d, $J_{6,7}$=4.5Hz, $J_{5,6}$=3Hz, 6-C$\underline{H}$), 5.14(d of d, $J_{trans}$=18Hz, $J_{gem}$=2Hz, vinylic-$\underline{H}$), 4.94(d of d, $J_{cis}$=10.8Hz, $J_{gem}$=2Hz, vinylic-$\underline{H}$), 4.58(bs, 1-C$\underline{H}$), 4.19(d, $J_{gem}$=4.5Hz, 7-C$\underline{H}$), 3.2(d, $J_{gem}$=17Hz, 12-C$\underline{H}$), 2.7-2.2 (m, —COC$\underline{H}_2$, —NC$\underline{H}_2$, 12-C$\underline{H}$), 2.3(s, N—C$\underline{H}_3$), 1.56, 1.42, 1.4, 1.1, 0.96(s, 5×C$\underline{H}_3$).

3. 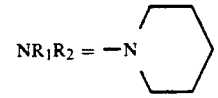
   $NR_1R_2 = -N$

PMR (CDCl$_3$): δ = 6.08(d of d, $J_{cis}$=10Hz, $J_{trans}$=17Hz, vinylic-$\underline{H}$), 5.9(d of d, $J_{6,7}$=4.5Hz, $J_{5,6}$=3Hz, 6-C$\underline{H}$), 5.14(d of d, $J_{trans}$=17Hz, $J_{gem}$=2Hz, vinylic-$\underline{H}$), 4.94(d of d, $J_{cis}$=10Hz, $J_{gem}$=2Hz, vinylic-$\underline{H}$), 4.58(bs, 1-C$\underline{H}$), 4.18(bs, collapse to d on D$_2$O addition J=4.5Hz, 7-C$\underline{H}$), 3.22(d, $J_{gem}$=17Hz, 12-C$\underline{H}$), 2.8-2.08(m, COC$\underline{H}_2$, N—C$\underline{H}_2$, 12-C$\underline{H}$), 1.6, 1.44, 1.4, 1.1, 0.96(s, 5×C$\underline{H}_3$).

4. 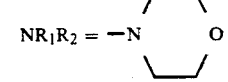
   $NR_1R_2 = -N\phantom{xx}O$

PMR (CDCl$_3$): δ = 6.08(d of d, $J_{cis}$=10Hz, $J_{trans}$=17Hz, vinylic-$\underline{H}$), 5.9(d of d, $J_{6,7}$=4.5Hz, $J_{5,6}$=3Hz, 6-C$\underline{H}$), 5.16(d of d, $J_{trans}$=17Hz, $J_{gem}$=2Hz, vinylic-$\underline{H}$), 4.94(d of d, $J_{cis}$=10Hz, $J_{gem}$=2Hz, vinylic-$\underline{H}$), 4.6(bs, 1-C$\underline{H}$), 4.2(d of d, $J_{6,7}$=4.5Hz, $J_{7,OH}$=6Hz, collapse to d, J=4.5 Hz, 7C$\underline{H}$), 3.7(t, J=5.4Hz, O—C$\underline{H}_2$), 3.02(d, $J_{gem}$=17Hz, 12-C$\underline{H}$), 2.88-2.2 (m, COC$\underline{H}_2$, N—C$\underline{H}_2$, 12-C$\underline{H}$), 1.6, 1.42, 1.4, 1.1, 0.98(s, 5×C$\underline{H}_3$).

We claim:

1. Process for the manufacture of 6β-(3-substituted amino)-propionyloxy-7-deacetyl-forskolin derivatives of the general formula I

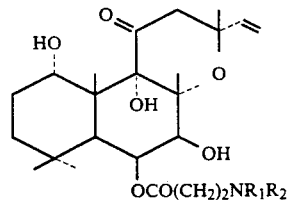

wherein
R$_1$ and R$_2$ each stands for hydrogen, alkyl, aryl, aralkyl or dialkylaminoalkyl; or
R$_1$ and R$_2$ together with the nitrogen to which they are attached form a heterocycle selected from the group consisting of morpholino, piperidino, pyrrolidino, piperazino, or homopiperidino, which may optionally be substituted at one or more positions by alkyl, alkoxy, hydroxyl, halogen or aryl and pharmaceutically acceptable salts thereof, which comprises
reacting in a one-pot reaction sequence 7-deacetyl forskolin of the formula II

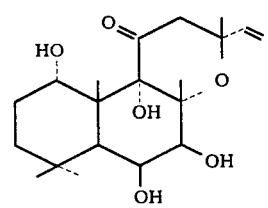

with a 3-halopropionylhalide in the presence of an organic base and treating the 6β-(3-halopropionyloxy) derivative thus obtained with aqueous acetonitrile and an alkali hydroxide, followed by treating the 6β-(3-halopropionyloxy) derivative with an amine of the formula

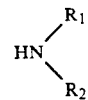

wherein R$_1$ and R$_2$ have the meaning given above and, if desired, converting the compounds of the formula I into their pharmaceutically acceptable salts.

2. Process as claimed in claim 1, wherein the amine is dimethylamine.

3. Process as claimed in claim 1, wherein the amine is piperidine.

4. Process as claimed in claim 1, wherein the amine is morpholine.

5. Process as claimed in claim 1, wherein the amine is N-methylpiperazine.

6. Process as claimed in claim 1, wherein the alkali hydroxide is sodium hydroxide.

* * * * *